(12) United States Patent
Bosch et al.

(10) Patent No.: US 7,714,169 B2
(45) Date of Patent: May 11, 2010

(54) CONTINUOUS PREPARATION OF ALKYLAMINES

(75) Inventors: Marco Bosch, Mannheim (DE); Roderich Röttger, Mannheim (DE); Bernd Stein, Alsbach-Hähnlein (DE); Thomas Krug, Worms (DE); Johann-Peter Melder, Böhl-Iggelheim (DE); Theodor Weber, Ludwigshafen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 12/258,563

(22) Filed: Oct. 27, 2008

(65) Prior Publication Data

US 2009/0088591 A1 Apr. 2, 2009

Related U.S. Application Data

(62) Division of application No. 10/536,498, filed as application No. PCT/EP03/13170 on Nov. 24, 2003, now abandoned.

(30) Foreign Application Priority Data

Nov. 26, 2002 (DE) ............................... 102 55 294

(51) Int. Cl.
*C07C 209/16* (2006.01)

(52) U.S. Cl. ....................... 564/479; 564/480
(58) Field of Classification Search ................. 564/479, 564/480
See application file for complete search history.

(56) References Cited

U.S. PATENT DOCUMENTS

| | | | |
|---|---|---|---|
| 2,660,598 A | 11/1953 | Hoffert | |
| 3,384,667 A | 5/1968 | Hamilton | |
| 4,339,413 A | 7/1982 | Lahne et al. | |
| 4,398,041 A | 8/1983 | Cochran et al. | |
| 4,485,261 A | 11/1984 | Ashina et al. | |
| 4,578,516 A | 3/1986 | Ashina et al. | |
| 4,582,936 A | 4/1986 | Ashina et al. | |
| 4,720,588 A | 1/1988 | Turcotte et al. | |
| 4,732,918 A | 3/1988 | Lohmueller et al. | |
| 4,918,234 A * | 4/1990 | Deeba .................. | 564/480 |
| 5,068,442 A | 11/1991 | Ashina et al. | |
| 5,382,696 A | 1/1995 | Kiyoura et al. | |
| 5,688,854 A | 11/1997 | Fujita et al. | |
| 6,294,633 B1 | 9/2001 | Hidaka et al. | |

FOREIGN PATENT DOCUMENTS

| | | |
|---|---|---|
| DE | 34 14 717 | 10/1985 |
| EP | 0 230 908 | 8/1987 |
| EP | 0 342 999 | 11/1989 |
| EP | 0 534 195 | 3/1993 |
| EP | 0 593 086 | 4/1994 |
| EP | 0 763 519 | 3/1997 |
| EP | 1 077 084 | 2/2001 |

OTHER PUBLICATIONS

Corbin, D. R. et al., "Methylamines Synthesis: A Review", Catalysis Today 37 (1997), pp. 71-102.

* cited by examiner

*Primary Examiner*—Brian J Davis
(74) *Attorney, Agent, or Firm*—Connolly Bove Lodge & Hutz LLP

(57) ABSTRACT

In the continuous process for preparing alkylamines by reacting $C_{1-4}$-alkanols with ammonia in the gas phase in the presence of a shape-selective fixed-bed catalyst in a cooled reactor, the shape-selective fixed-bed catalyst is present in a single contiguous fixed bed in the reactor and tubes through which coolants are passed run within the fixed bed to regulate the temperature of the fixed bed.

4 Claims, No Drawings

CONTINUOUS PREPARATION OF ALKYLAMINES

This application is a divisional of U.S. patent application Ser. No. 10/536,498, filed May 25, 2005 which is now abandoned, which claims benefit to the national stage application (under 35 U.S.C. 371) of PCT/EP2003/013170 filed Nov. 24, 2003 which claims benefit to German application 102 55 294.0 filed Nov. 26, 2002.

The present invention relates to a reactor and a process for preparing alkylamines by reacting $C_{1-4}$-alkanols with ammonia in the gas phase in the presence of a shape-selective fixed-bed catalyst.

In particular, the invention relates to the reaction of methanol with ammonia to produce methylamines, preferably in a selectivity to dimethylamine (DMA) which is greater than that resulting from the thermodynamic equilibrium.

The classical synthesis of monomethylamine (MMA), dimethylamine (DMA) and trimethylamine (TMA) is carried out from ammonia and methanol in the gas phase over amorphous non-shape-selective silica-alumina (mixed forms of aluminum and silicon oxides) at pressures of from 15 to 50 bar. When relatively high temperatures (350 to about 500° C.) are employed, thermodynamic equilibrium is established or approximately established over these heterogeneous catalysts provided that the residence time in the reactor at the given pressure and given feed temperature is sufficient. A characteristic of these "equilibrium catalysts" is a proportion of trimethylamine in the output from the reactor of from 40 to 60% by weight based on the sum of monomethylamine, dimethylamine and trimethylamine. The product distribution is dependent on the temperature and on the N/C ratio. The proportion of trimethylamine in the product mixture can be reduced when a relatively large excess of ammonia (relatively large N/C ratio) is present in the reaction mixture. If the proportion of monomethylamine and/or dimethylamine in the desired product mixture taken off after the known work-up is greater than that corresponding to the output from the reactor, both the excess trimethylamine and the unreacted ammonia have to be recirculated to the reactor, resulting in large circulations of ammonia and trimethylamine.

The worldwide consumption of TMA is from about 10 to 20% by weight of the total amount of methylamines consumed. It is desirable to increase the proportion of DMA and MMA without recirculation of the reaction mixture. This is achieved by the use of shape-selective zeolite catalysts such as mordenite, ZK-5, Rho, erionite, chabazite, ferrierite and clinoptilolite at from 250 to 400° C. This gives a product mixture comprising predominantly dimethylamine and monomethylamine and containing only little trimethylamine. According to EP-A-1 077 084, a methanol conversion of 99.2% and an MMA/DMA/TMA weight ratio of 32/52/16 in the product mixture are measured over a shape-selective H-mordenite catalyst at an N/C ratio of 1.9, a reaction pressure of 20 bar, a temperature of 320° C. and a GHSV of 2500 $h^{-1}$ after 6 hours. If dimethylamine forms the major part of the desired product mixture taken off after the known work-up, the quantities which have to be separated off by distillation and recirculated to the reactor can be reduced significantly compared to the synthesis over non-shape-selective "equilibrium catalysts".

Studies on the selectivity to dimethylamine when using shape-selective mordenite catalysts have shown that the proportion of DMA is about 60% by weight at 320° C. and an N/C ratio of from 1.2 to 2.0. Since the amount of ammonia can be varied without altering the selectivity, it is desirable to set a small N/C ratio, since then less ammonia has to be separated off by distillation and recirculated to the reactor or a second reactor using an "equilibrium catalyst". The use of N/C ratios of less than 0.8 should be avoided, since the formation of by-products which deactivate the catalyst (carbonization) occurs.

The operating life of the zeolite catalyst is better, the smaller the difference between outlet temperature and inlet temperature of the reactor, preferably less than 60° C. Excessively high output temperatures or "hot spots" in the reactor lead to a decrease in the proportion of DMA in the product mixture and an increase in the proportion of TMA. U.S. Pat. No. 4,398,041 describes a process in which the reactor feed is diluted with excess ammonia to reduce the temperature increase in the adiabatically operated reactor. The large excess of ammonia (N/C ratio of $\geq 2.0$) results in the considerable disadvantage that large amounts of ammonia have to be separated off by distillation and recirculated to the reactor.

For this reason, a mode of operation in which all or part of the heat generated by the reaction is removed by means of heat exchangers installed in the reactor in order to limit the difference between outlet temperature and inlet temperature is more advantageous in the synthesis of methylamines using shape-selective zeolite catalysts. EP-B-0 763 519 describes the synthesis of methylamines in one or more reactors which is/are divided into two or more individual beds which are arranged in parallel or in series. Heat removal is achieved by cooling the reaction mixture between these individual beds. The parallel arrangement of individual beds between which a heat-removing medium is present is achieved, for example, by means of shell-and-tube reactors.

The synthesis of methylamines in shell-and-tube reactors is also described in EP-A-0 593 086.

In shell-and-tube reactors, the catalyst bed and the reaction mixture are located within the tubes and the cooling medium is present outside the tubes. In the synthesis of methylamines, the pressure in the reaction medium is generally from 15 to 25 bar. At a synthesis temperature of 320° C., the pressure of the cooling medium is about 100 bar when boiling water is used for cooling. The design pressure of the reactor wall of a shell-and-tube reactor therefore has to be about 100 bar.

It is an object of the present invention to provide reactors and processes for preparing alkylamines by reacting alkanols with ammonia in the gas phase in the presence of shape-selective fixed-bed catalysts, which avoid the disadvantages of the existing processes and, in particular, require a smaller outlay in terms of apparatus.

We have found that this object is achieved by a continuous process for preparing alkylamines by reacting $C_{1-4}$-alkanols with ammonia in the gas phase in the presence of a shape-selective fixed-bed catalyst in a cooled reactor, wherein the shape-selective fixed-bed catalyst is present in a single contiguous fixed bed in the reactor and tubes through which coolants are passed run within the fixed bed to regulate the temperature of the fixed bed.

It has been found that the configuration of a fixed-bed reactor for the synthesis of alkylamines can be chosen so that the catalyst bed forms a single contiguous bed in which or between which tubes within which the cooling medium is present are located. The advantage is that the design pressure of the cylindrical reactor wall and the reactor caps only has to correspond to the product-side pressure. Only the tubes in which the cooling medium is present have to be designed for the higher pressure of the cooling medium. The facilities for distributing, collecting and leading away the cooling medium likewise have to be designed for this pressure. The wall thickness of the reactor wall can be significantly reduced in this way, which leads to significantly lower costs and to a significantly lower weight of the reactor. The tubes for the cooling medium are advantageously used in coiled form, since in this design stresses due to different thermal expansions of the wall of the apparatus and cooling tubes are virtually insignificant. A combination of this reactor design with shape-selective catalysts gives particular advantages.

According to the present invention, the tubes can have any suitable or desired geometry. The tubes preferably have a cross section which does not have any corners. For example, the tube cross section can be circular or ellipsoidal. The tube diameter is preferably from 1 to 5 cm.

Suitable reactors are described, for example, in EP-A-0 534 195. They can be used, inter alia, for the preparation of methylamines from methanol and ammonia.

Any suitable coolant which allows efficient uptake and removal of heat and efficient transport of the cooling medium can be passed through the tubes. Suitable coolants are, for example, water, aqueous solutions containing, for example, glycols or salt melts. Cooling is preferably carried out by means of boiling water cooling, so that the coolant is water or comprises predominantly water.

The pressure in the coolant is preferably from 40 to 220 bar, particularly preferably from 60 to 150 bar, and the pressure in the fixed catalyst bed is from 10 to 50 bar, particularly preferably from 15 to 30 bar. For example, the product-side pressure in the reactor can be about 25 bar, while the pressure of the cooling medium can be about 100 bar in the case of boiling water cooling.

The geometry of the arrangement of the coolant tubes in the reactor can be chosen freely, as long as efficient heat removal is achieved. The geometry is preferably chosen so that the temperature distribution in the fixed catalyst bed is very uniform. The design and operation of are preferably such that the difference between outlet temperature and inlet temperature of the reactor is less than 60° C., particularly preferably less than 35° C.

Suitable reactors are, for example, Linde isothermal reactors or comparable nickel reactors as are also described in DE-A-34 14 717 and EP-A-0 534 195. They are usually operated isothermally.

Suitable dimensions of the reactor and the tubes for the coolant are known to those skilled in the art.

The invention also provides a reactor for the reaction of $C_{1-4}$-alkanols with ammonia in the gas phase for preparing alkylamines, which comprises a shape-selective fixed-bed catalyst which is present as a single contiguous fixed bed in the reactor and through whose interior tubes through which a coolant can be passed run.

The reactor is preferably made of metallic materials such as stainless steel. The wall thicknesses are chosen so that the above-described pressure conditions are possible.

In the reactor, the catalyst bed forms a single contiguous bed. This means that there are no individual regions or islands in the catalyst bed in the reactor but instead the entire bed is contiguous.

The object of the invention is also achieved by a continuous process for preparing alkylamines by reacting $C_{1-4}$-alkanols with ammonia in the gas phase in the presence of a shape-selective fixed-bed catalyst in a reactor in which part of the $C_{1-4}$-alkanols, the ammonia or mixtures thereof introduced into the reactor is fed into the fixed catalyst bed at at least one point at which a previously reacted reaction mixture of $C_{1-4}$-alkanols and ammonia which has a temperature higher than that of the $C_{1-4}$-alkanols, ammonia or mixtures thereof fed in is present.

In this embodiment, part of the reactor feed mixture or part of the individual components fed in is not introduced at the inlet of the reactor but is instead added to the previously partially reacted reaction mixture in the interior of the reactor, preferably in the first ⅔ of the catalyst bed. The temperature of the portions added in the interior is lower than the temperature of the previously partially reacted reaction mixture at the point in the reactor at which the addition takes place. Preference is given to from 30 to 90%, particularly preferably from 50 to 80%, of the starting materials to be introduced into the reactor being introduced not at the inlet of the reactor but in the interior of the reactor. The temperature of the added starting materials is preferably at least 40° C., particularly preferably at least 70° C., lower than the temperature prevailing in the catalyst bed at the point of addition. The introduction can be carried out at one or more points along the catalyst bed. The introduction is preferably regulated so that a largely homogeneous temperature distribution is established in the entire catalyst bed. The amount of starting materials fed into the catalyst bed can thus be used to take up the energy of reaction which is liberated.

Furthermore, the object of the present invention is achieved by a continuous process for preparing alkylamines by reacting $C_{1-4}$-alkanols with ammonia in the gas phase in the presence of a shape-selective fixed-bed catalyst in a reactor, in which part of the $C_{1-4}$-alkanols, the ammonia or mixtures thereof is introduced in liquid form into the reactor in such a way that vaporization takes place on the fixed catalyst bed. In this embodiment, part of the reactor feed mixture or part of the individual components being fed in is introduced in liquid form. The liquids vaporize in the reactor or on the fixed-bed catalyst. Preference is given to from 5 to 70%, particularly preferably from 10 to 50%, of the total starting materials to be fed into the reactor being introduced in liquid form. Suitable devices for feeding in the liquid starting materials are known. The fixed catalyst bed can be cooled by take up of heat at the point of addition.

Furthermore, the object of the present invention is achieved by a continuous process for preparing alkylamines by reacting $C_{1-4}$-alkanols with ammonia in the gas phase in the presence of a shape-selective fixed-bed catalyst in a reactor, wherein a heat transfer medium which is inert toward the $C_{1-4}$-alkanols and ammonia and the reaction products and/or does not significantly affect the activity and selectivity of the catalyst is additionally fed into the fixed catalyst bed. Here, one or more other components are added to the reactor feed mixture in an amount which is able to take up part of the heat generated in the reaction. The added component is chemically inert toward the other components in the synthesis of alkylamines and/or does not influence the selectivity of the reaction. It preferably has no effect or no significant effect on the activity and selectivity of the catalyst. For example, water or an aqueous solution having a water content of at least 50%, preferably at least 80%, is used as heat transfer medium.

The amount of heat transfer medium added depends on the practical requirements of heat removal in the reactor. The heat transfer medium can be separated off from the product stream in a simple manner by suitable methods such as distillation.

The process of the present invention is carried out using $C_{1-4}$-alkanols, preferably $C_{1-2}$-alkanols, in particular methanol, which are reacted with ammonia. The N/C ratio, i.e. the ratio of the number of N atoms to C atoms, when methanol is used is preferably from 0.8 to 3.5, particularly preferably from 1.0 to 2.5, in particular from 1.2 to 2.0. According to the present invention, this makes it possible to prevent relatively large ammonia recycled streams occurring. In addition, the formation of by-products which can deactivate the catalyst can be prevented.

According to the present invention, shape-selective catalysts, in particular zeolites, are used. It is also possible to use silicoaluminophosphates (SAPOs). Examples of suitable shape-selective catalysts are mordenite, ZK-5, Rho-zeolite, erionite, chabazite, ferrierite, clinoptilolite, SAPO-34, ZSM-5, ZSM-11, ZSM-21, ZSM-35, NU-85, offretite, Y-zeolite and further catalysts as are described in Catalysis Today 37 (1997), pages 71 to 102, especially Table 4 on page 76. The other shape-selective catalysts mentioned in this reference can also be used. As regards modified zeolite catalysts (mordenites), reference may be made to U.S. Pat. No. 4,485,261, U.S. Pat. No. 4,578,516, U.S. Pat. No. 4,582,936 and EP-A-0 342 999. These are modified zeolites which are derived from natural or synthetic mordenites and have been chemically modified to adjust the cation content, in particular the content of alkali metal ions and alkaline earth metal ions, and have subsequently been treated with steam. Further suitable mordenite catalysts are disclosed in EP-A-1 077 084. That document, like U.S. Pat. No. 4,398,041, EP-A-0 593 086 and EP-A-0 763 519 indicates suitable reaction conditions. When shape-selective zeolite catalysts are used, the reaction is preferably carried out in the temperature range from 200 to 500° C., particularly preferably from 250 to 400° C. The reaction pressure is preferably from 5 to 50 bar, particularly preferably from 10 to 40 bar, in particular from 15 to 30 bar.

The space velocity over the catalyst (GHSV) is preferably from 250 to 5000 standard $l/l_{cat}h$.

According to the present invention, the catalyst is used in the form of a fixed bed made up of catalyst particles/shaped bodies. The catalyst particles can have any geometry, for example extrudates, pellets, prills or granules. The catalyst can consist entirely of active component or can contain from 1 to 60% by weight of binder. Customary binders are oxides of the elements aluminum, silicon, titanium and zirconium and also clays such as montmorillonite and kaolin.

Various embodiments of the present invention have been described above. These embodiments can also be combined with one another. For example, the catalyst arrangement according to the present invention and the introduction of starting materials or cooling media at various points in the reactor can be combined with one another. The introduction of starting materials and cooling media can also be combined.

The $C_{1-4}$-alkanols, ammonia or mixtures thereof introduced into the reactor can be fed in radially to the longitudinal axis of the reactor, i.e. centripedally. Such an embodiment is described, for example, in EP-A-0 534 195.

Preference is given to a reaction in which the difference between inlet temperature and outlet temperature is less than 60° C., preferably less than 35° C., the N/C ratio is in the range from 0.8 to 3.5, preferably from 1.0 to 2.5, in particular from 1.2 to 2.0, and shape-selective zeolite catalysts are used.

The process of the present invention makes it possible, in particular, to prepare methylamines from methanol and ammonia with a high selectivity to dimethylamine.

We claim:

1. A continuous process for preparing alkylamines which comprises reacting $C_{1-4}$-alkanols with ammonia in the gas phase in the presence of a shape-selective fixed-bed catalyst in a cooled reactor, wherein the shape-selective fixed-bed catalyst is present in a single contiguous fixed bed in the reactor and tubes through which coolants are passed run within the fixed bed to regulate the temperature of the fixed bed, wherein the difference between outlet temperature and inlet temperature of the reactor is less than 60° C.

2. The process as claimed in claim 1, wherein cooling is carried out by means of boiling water cooling.

3. The process as claimed claim 1, wherein the pressure in the coolant is from 40 to 220 bar and the pressure in the fixed catalyst bed is from 10 to 50 bar.

4. The process as claimed in claim 1, wherein the reactor has an inlet and an outlet and the difference between the outlet and inlet temperature is less than 35° C.

* * * * *